United States Patent [19]
Hara

[11] Patent Number: 5,685,311
[45] Date of Patent: Nov. 11, 1997

[54] IMAGE DISPLAY SYSTEM

[75] Inventor: Makoto Hara, Hachioji, Japan

[73] Assignee: Olympus Optical Company, Ltd., Tokyo, Japan

[21] Appl. No.: 543,044

[22] Filed: Oct. 13, 1995

[30]  Foreign Application Priority Data

Oct. 20, 1994 [JP] Japan .................................. 6-255358
Sep. 21, 1995 [JP] Japan .................................. 7-242769

[51] Int. Cl.$^6$ ........................................................ A61B 8/00
[52] U.S. Cl. ............................ 128/662.03; 128/662.06
[58] Field of Search ..................... 128/662.03, 661.01, 128/662.06; 310/334–336; 29/25.35

[56]  References Cited

U.S. PATENT DOCUMENTS

| | | | |
|---|---|---|---|
| 4,641,660 | 2/1987 | Bele | 128/661.01 |
| 4,686,408 | 8/1987 | Ishiyama | 310/335 X |
| 4,783,888 | 11/1988 | Fujii et al. | 29/25.35 |
| 4,962,332 | 10/1990 | Rokurohta et al. | 73/632 |
| 5,027,822 | 7/1991 | Gelly et al. | 128/661.01 |
| 5,042,493 | 8/1991 | Saito et al. | 128/662.03 |
| 5,044,053 | 9/1991 | Kopel et al. | 29/25.35 |
| 5,044,370 | 9/1991 | Dubut et al. | 128/662.03 |
| 5,186,177 | 2/1993 | O'Donnell et al. | 128/661.01 X |
| 5,456,259 | 10/1995 | Barlow et al. | 128/662.03 |

FOREIGN PATENT DOCUMENTS

| | | |
|---|---|---|
| 2-40899A | 2/1987 | Japan . |
| 1-136500A | 5/1989 | Japan . |
| 4-166139A | 6/1992 | Japan . |

*Primary Examiner*—Francis Jaworski

[57]  ABSTRACT

An ultrasonic probe having an electronic radial transducer is disclosed. In the ultrasonic probe, a plurality of piezoelectric elements having electrodes on both surfaces thereof are arranged and juxtaposed on a circular backing member. A doughnut shaped substrate is provided on an end surface of the piezoelectric elements of the electronic radial transducer and having connection points arranged in a signal pattern conductive to one each electrode of the piezoelectric elements. Additionally, at least one overlapping substrate having connection points arranged in accordance with the respective connection points of the signal pattern of the doughnut shaped substrate.

15 Claims, 12 Drawing Sheets

FIG_3a

FIG_3b

FIG_4

FIG_8

FIG_9

FIG.10

FIG_11a

FIG_11b

FIG_14a

FIG_14b

IMAGE DISPLAY SYSTEM

BACKGROUND OF THE INVENTION

1. Field of the Invention

The present invention relates to an electronic radial scanning ultrasonic probe comprising a plurality of piezoelectric elements disposed at outer periphery surface of a cylinder and capable of obtaining a tomographic image on a plane perpendicular to an insertion axis of the cylinder. More particularly, to an ultrasonic probe in which a method of connecting respective transducer elements and a signal transmitting coaxial cable is improved.

2. Description of the Related Art

An electronic scanning ultrasonic probe has been provided to an insertion section of an endoscope which is inserted into a body cavity of a patient. By using this ultrasonic probe, a deep organ such as digestive tube wall and pancreas or the like can be displayed clearly with good image quality without subjecting to effects of gaseous in the body cavity and bones of the patient. A transducer of these electronic scanning ultrasonic probe has more than tens of transducer elements, so that signal transmitting and receiving coaxial cables of the number corresponding to the number of respective transducer elements must be utilized.

In case of connecting electrodes of respective transducer elements of the electronic scanning ultrasonic probe to signal transmitting and receiving coaxial cables, methods of soldering core lines of the coaxial cables to signal electrodes of respective transducer elements and of soldering shield lines of the coaxial cables to ground electrodes of respective transducer elements are commonly utilized.

For this soldering connection, the technique that electrodes of respective transducer elements are adhered to patterns of a flexible substrate having the conductive patterns of the number corresponding to that of these electrodes so as to widen the pitches of signal lines, is disclosed in for example Japanese patent application Opened Nos. 40,899/87, 136,500/89 and 166,139/92.

In the ultrasonic probe for performing ultrasonic diagnosis by inserting it into the body cavity, due to the limit for the outer diameter of the ultrasonic probe, in case of connecting a plurality of coaxial cables, following problems arise.

First, the ultrasonic probes shown in Japanese patent application Opened No. 136,500/89, or the like have a complicated shape and perform an operation for connecting tens of the coaxial cables to respective transducer elements by soldering or the like in the region limited thinly, shortly and very narrowly to the extent capable of inserting it in the body cavity. As a result this connecting operation takes considerable time and needs technical skills. In such an ultrasonic probe, repair and maintenance thereof are substantially impossible.

Additionally, since a number of tubes such as glass fiber bundle for imaging device and illuminating purpose or air/water supply tubes are incorporated in a tube having thin inner diameter of about 12 mm, it is difficult to provide a space in which the flexible substrate is incorporated as shown in Japanese patent application (Opened No. 40,899/87) or the like. Indeed even if such a space can be provided, the length of tip hard section is too and thus it is unsuitable to perform ultrasonic diagnosis by inserting it into the body cavity.

SUMMARY OF THE INVENTION

It is an object of the present invention to eliminate the above described disadvantages of the conventional ultrasonic probe.

It is another object of the present invention to provide an ultrasonic probe having superior assemblage and repairability in construction which is capable of connecting respective transducer elements to coaxial cables in a narrow limited space such as an endoscope.

It is other object of the present invention to provide an ultrasonic probe capable of limiting the length of tip hard section of the ultrasonic probe due to occupation of the cable connecting section.

According to the present invention, there is provided an ultrasonic probe having an electronic radial transducer in which a plurality of series of piezoelectric elements having electrodes provided on both major surfaces thereof are arranged and juxtaposed on a circular backing member comprising a doughnut type substrate provided on an end surface in the inserting direction of the piezoelectric element series of the electronic radial transducer and having signal pattern conductive to one electrode of the piezoelectric element, and at least one substrate having a pattern formed so as to be conducted corresponding to respective signal patterns of the doughnut type substrate.

According to the present invention, a plurality of cable series connected to the signal patterns of the substrate are disposed on the inner side of the doughnut shaped substrate.

In an embodiment of the image display system according to the present invention, at least one of the substrates have patterns formed so as to conduct opposite to respective signal patterns of the doughnut shaped substrate and is a flexible substrate.

The signal patterns of the doughnut shaped substrate are disposed in a radial configuration. The shape of the substrate is a fan shape, or a paper-stripe, or a doughnut shape. The fixing of the substrate and the doughnut shaped substrate are performed by the adhering due to soldering or conductive adhesive, or the welding of the cap provided on the tip portion in the inserting direction of the electronic radial transducer. The cable is a coaxial cable of less than 0.3 mm in outer diameter.

According to the present invention, an ultrasonic probe further comprises a tip hard section of the probe which has a large diameter cylindrical portion and a small diameter cylindrical portion, an ultrasonic transducer fitted on the small diameter cylindrical portion of the tip hard section, and a tip cap section having a small diameter cylindrical portion which is inserted and fitted into an axial cylindrical hole of the hard section, the plural series of the cables inserted in the axial cylindrical hole of the hard section being fixed on the outer periphery surface of the small diameter cylindrical portion by a first rubber member, and the upper end portion bent in the radial direction of the substrate and connected to the cable group being fixed to the doughnut shaped substrate through a second rubber member by the tip cap section.

According to the present invention, the cable can be connected to the electronic radial transducer with superior efficiency and then the length of the tip hard section of the endoscope can be decreased.

BRIEF DESCRIPTION OF THE DRAWINGS

FIG. 3b is an explanatory view showing a cross-sectional view taken on line B—B of FIG. 3a;

FIG. 4 is a perspective view explaining a connection method for the coaxial cable shown in FIG. 3a;

FIG. 11b is a cross-sectional view taken on line D—D of FIG. 11a;

FIG. 13b is a cross-sectional view taken on line E—E of FIG. 13a;

FIG. 13c is a cross-sectional view taken on line F—F of FIG. 13a;

DETAILED DESCRIPTION OF THE PREFERRED EMBODIMENTS

Referring to the drawings, there are shown various embodiments of an ultrasonic probe according to the present invention. Like parts are shown by corresponding reference characters throughout several views of the drawings.

Figure 1:
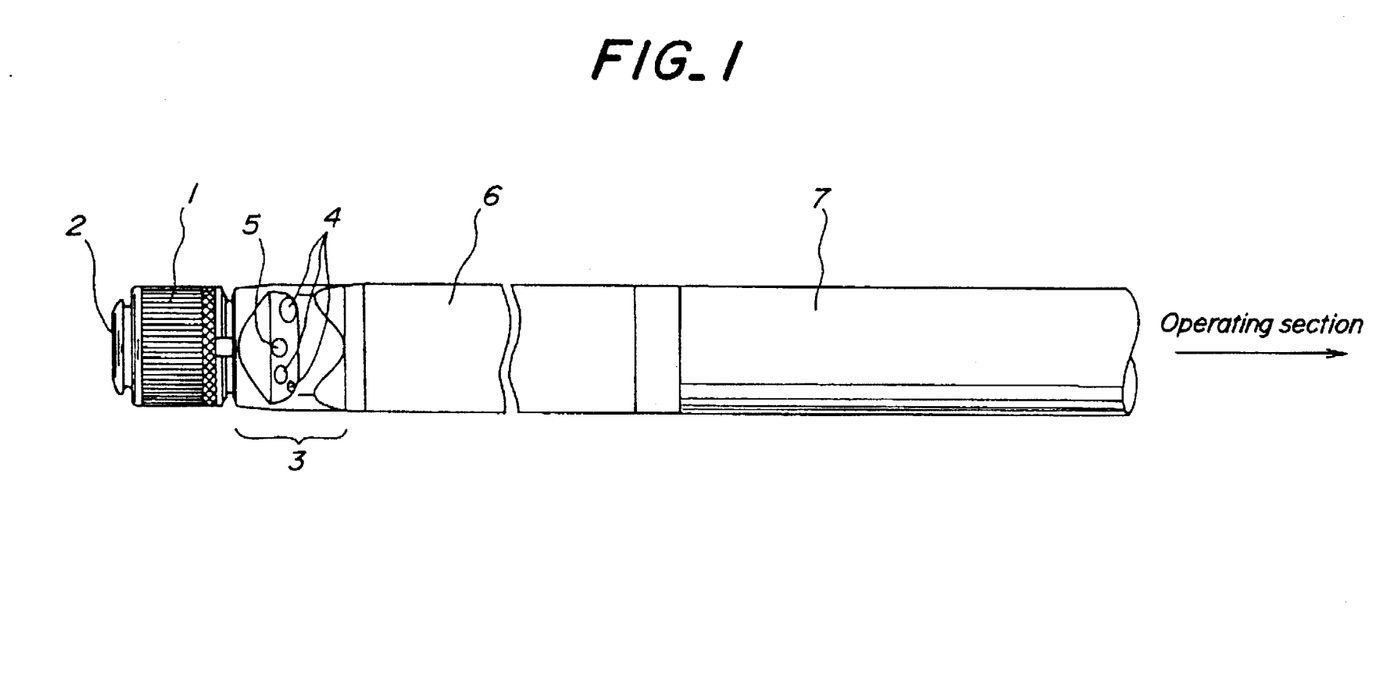
FIG. 1 is a side view showing a construction of a tip insertion section of a first embodiment of an ultrasonic probe according to the present invention.

FIG. 1 shows a construction of a tip insertion section of a first embodiment of an ultrasonic probe according to the present invention. In the first embodiment, the ultrasonic probe is provided on the insertion section of an ultrasonic endoscope of an electronic radial type, and an ultrasonic transducer 1 is provided on the tip of the probe. The tip in inserting direction of the ultrasonic transducer 1 (the left end thereof) is provided with for example a cap 2 of resin with a balloon channel. The ultrasonic transducer 1 is also divided so as to obtain an ultrasonic image in a plane orthogonal to an insertion axis, so that the back end of the ultrasonic transducer 1 (the right end thereof) is connected to a hard section 5 having an observation optical system 3 and an air/water supply channel 4, which are coupled to a bending section 6 which is coupled to a flexible tube 7, which is, connected to an operating section (not shown).

Figure 2A:
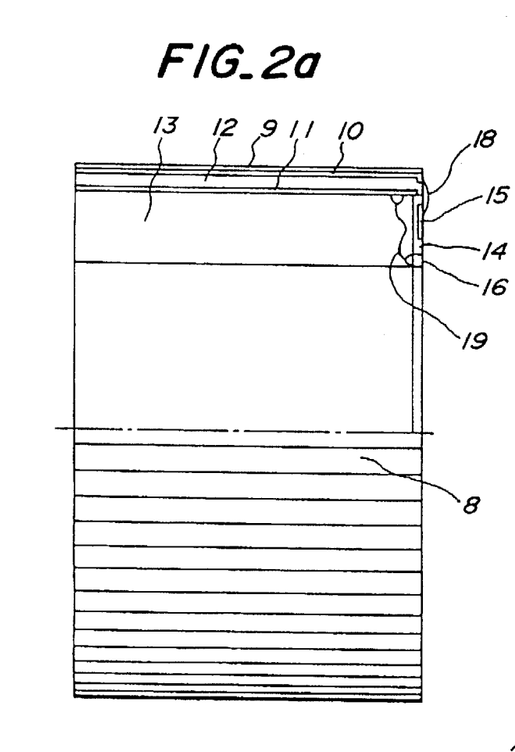
FIG. 2a is an elevational view partly in section showing the construction of the portion including an ultrasonic transducer of the probe according to the present invention.
Figures 2B, 2C:
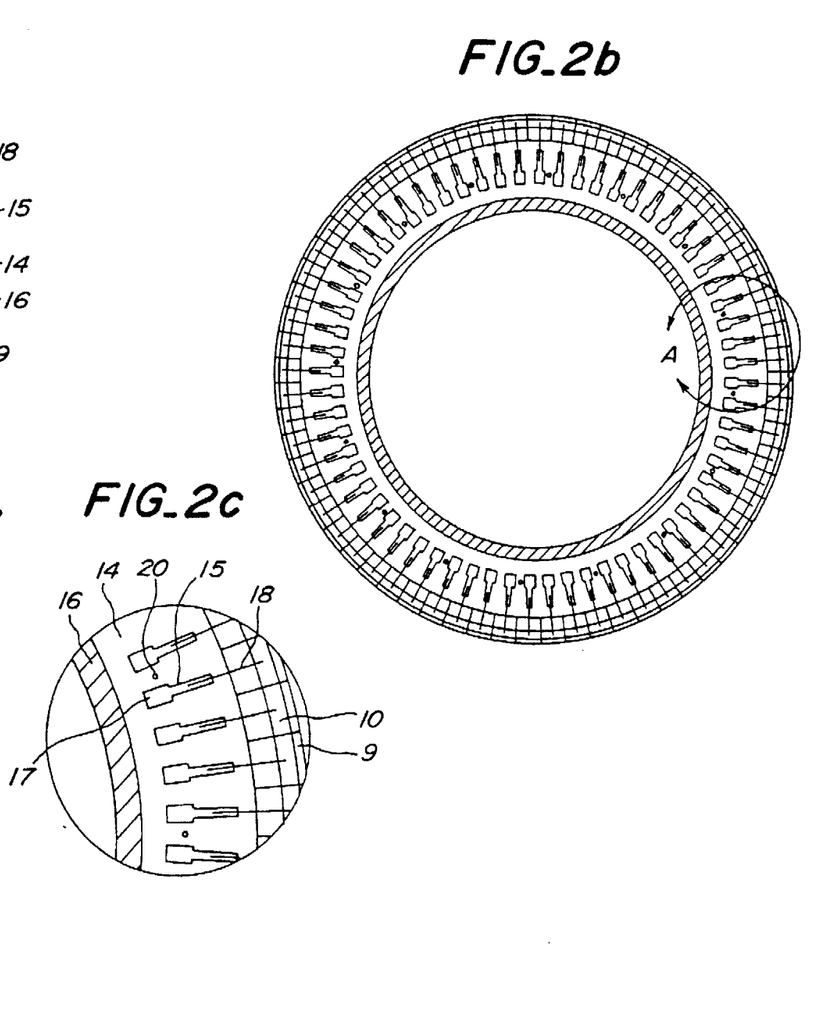
FIG. 2b is an end view showing the construction of the portion including an ultrasonic transducer of the probe according to the present invention.
FIG. 2c is a detailed explanatory view of an enclosed portion A shown in FIG. 2b.

FIGS. 2a to 2c show a portion including the ultrasonic transducer 1 therein. FIG. 2a shows an upper half portion in a cross-sectional view and a lower half section in a plan view. The outer surface of respective transducer elements 8 is enclosed by an adjusting layer 9. The element 8 includes a piezoelectric ceramics 12 (for example PZT) sandwiched by an upper electrode (SIGNAL) 10 and a lower electrode (GND) 11 and thus the lower portion of the lower electrode (GND) 11 is provided with a backing member 13. The ultrasonic transducer 1 is divided and arranged so as to scan the plane orthogonal to the inserting direction, so that the tip side end surface of the ultrasonic transducer 1 is provided with a doughnut shaped substrate 14 for the backing member 13 by an adhesive agent.

As shown in FIG. 2b and FIG. 2c which is an enlarged figure of section A of FIG. 2b, the doughnut shaped substrate 14 is provided with signal patterns 15 corresponding to respective elements 8 and which are printed radially equidistant and with ground pattern 16 printed concentrically near the center axis of the ultrasonic transducer. The central side end portion of the signal pattern 15 is provided integrally with a contacting point 17 substantially wider than the width of the signal pattern 15. This signal pattern 15 is electrically connected to the upper electrode 10 with a wire bonding 18, and the ground pattern 16 is electrically connected to the lower electrode 11 by soldering it to a lead wire 19, or by welding with conductive welding agent. The doughnut shaped substrate 14 is provided with a positioning projection 20 for positioning a fan shaped flexible substrate 22 shown in FIG. 3a on the same circular periphery with a certain distance.

Figure 3A:
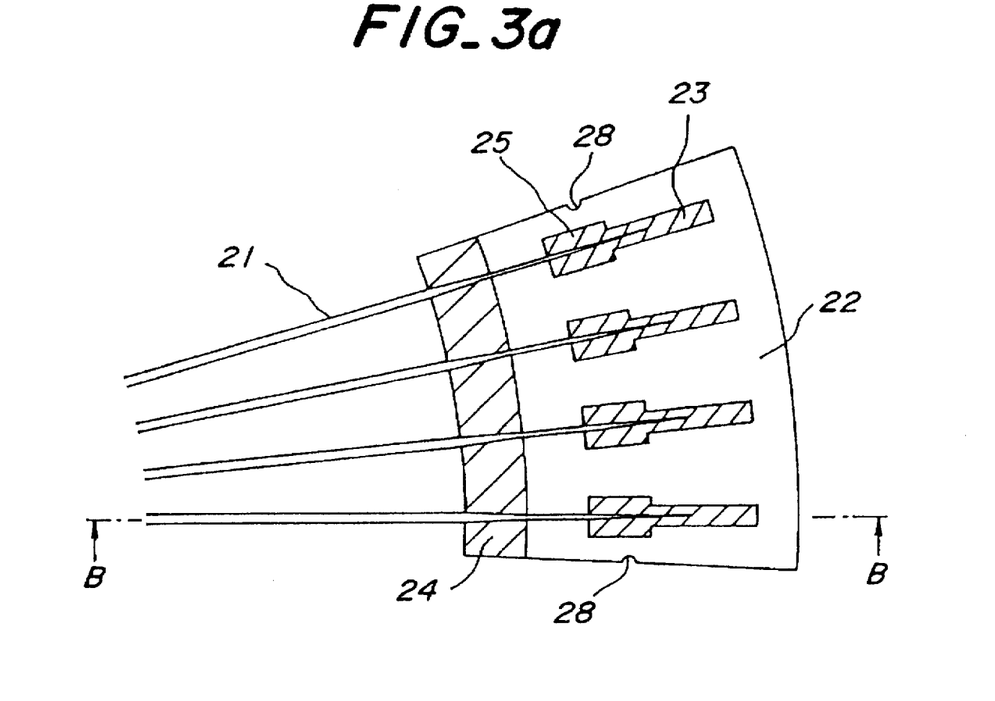
FIG. 3a is a coaxial cable series with a flexible substrate for using the ultrasonic probe according to the present invention.
Figure 3B:
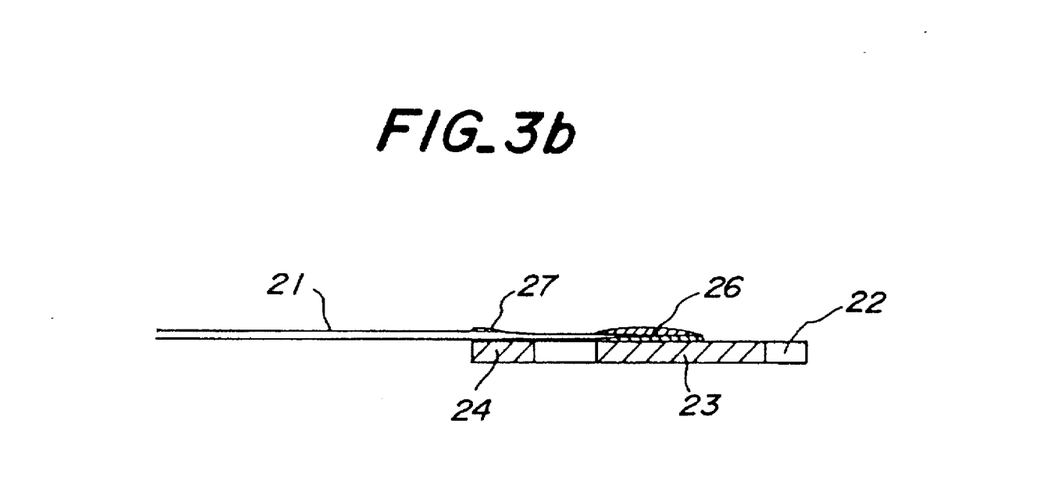

FIG. 3a is a detailed explanatory view showing groups of the coaxial cables with a flexible substrate used in the ultrasonic probe according to the present invention, and FIG. 3b is a cross-sectional view taken on line B—B of FIG. 3a. In FIGS. 3a and 3b, reference numeral 21 is a coaxial cable extended from a contacting connector for an ultrasonic observing device (not shown). The end portion of the coaxial cable 21 is connected to a fan shaped flexible substrate 22. The fan shaped flexible substrate 22 is provided with signal patterns 23 printed radially and equidistantly and ground pattern 24 printed concentrically at central side end portion of the fan. The signal patterns 23 printed on the fan shaped flexible substrate 22 are formed as the same patterns of signal patterns of the doughnut shaped substrate 14. The signal patterns 23 and ground pattern 24 are formed so as to become conductive at the rear surface of the fan shaped flexible substrate 22.

The signal patterns 23 are provided at their central side end portion with contact points 25 for performing an electrical connection to the connection points 17 of the doughnut shaped substrate 14. The signal patterns 23 are electrically connected to core wires 26 of the coaxial cables 21 by soldering or welding them with a conductive adhesive material. Shielding wires 27 of the coaxial cables 21 are electrically connected to the ground pattern 24 by soldering or welding them with a conductive adhesive material. The fan shaped flexible substrate 22 is provided at its side portion with positioning semicircular holes 28 in the case of the welding to the doughnut shaped substrate 14, and the inner diameter of the semicircular holes 28 is the same as that of the positioning projection 20.

Then, the method of connecting the coaxial cable in the first embodiment is explained with reference to FIG. 4.

Figure 4:
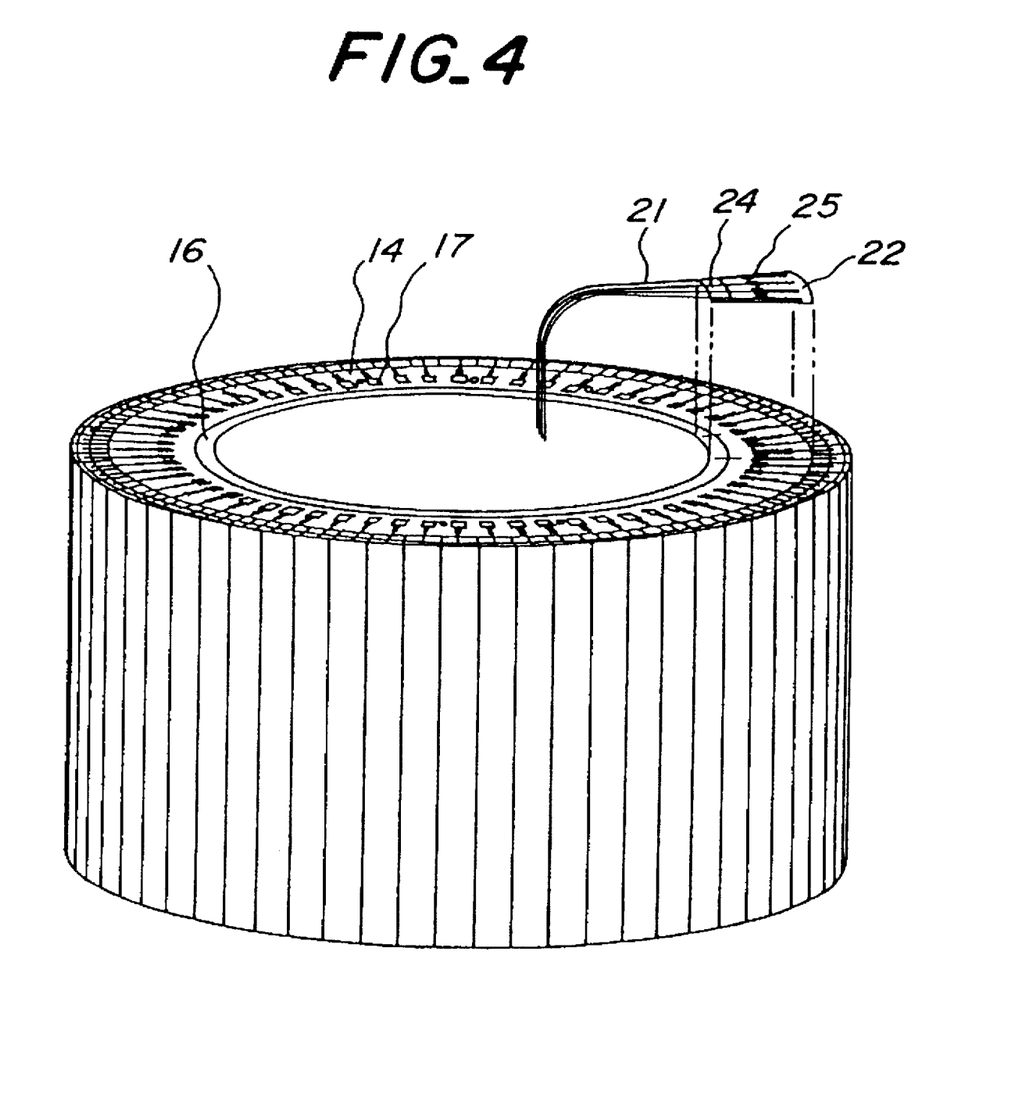

FIG. 4 explains a method of connecting the ultrasonic transducer 1 to the coaxial cable 21 with the flexible substrate. In this case, as shown in FIG. 3, the coaxial cable 21 is connected to the fan shaped flexible substrate 22 by soldering or welding them with a conductive adhesive material.

As shown in FIG. 4, the coaxial cable 21 with the flexible substrate is extended through the hole in the central portion of the ultrasonic transducer 1 and projected from the central portion of the doughnut shaped substrate 14. Then, the positioning semicircular holes 28 of the fan shaped flexible substrate 22 are fitted onto the positioning projection 20 of the doughnut shaped substrate 14, and then contacting points 25 of the fan shaped flexible substrate 22 are electrically connected to contacting points 17 of the doughnut shaped substrate 14 by soldering or welding them with a conductive adhesive material such that points 25 and 17 are superimposed with each other. Moreover, the ground pattern 24 of the fan shaped flexible substrate 22 is electrically connected to the ground pattern 16 of the doughnut shaped substrate 14 through soldering or welding of a conductive adhesive material.

After the above-mentioned steps, the cap section 2 is welded to the ultrasonic transducer 1 (see FIG. 1), and the assembly of the ultrasonic transducer 1 to the tip hard section 5 was completed.

According to the above ultrasonic probe of the first embodiment, following function and effect can be obtained.

At first, after removing the cap 2, the fitting condition of the doughnut shaped substrate 14 and the fan shaped flexible substrate 22 to remove the ultrasonic transducer 1 easily.

Secondly, the electric connection of the ultrasonic transducer 1 can be performed easily by connecting the doughnut shaped substrate 14 and the fan shaped flexible substrate 22 with the above connecting method.

Thirdly, it is possible to provide the connection method of the cable having superior assemblage and repairability in construction by the above first and second functions and effects.

Fourthly, the connection points of the cable are disposed between the ultrasonic transducer 1 and the cap 2, so that the outer diameter of the tip hard section of the endoscope can be decreased and the length of the tip hard section can be decreased.

Figure 5:
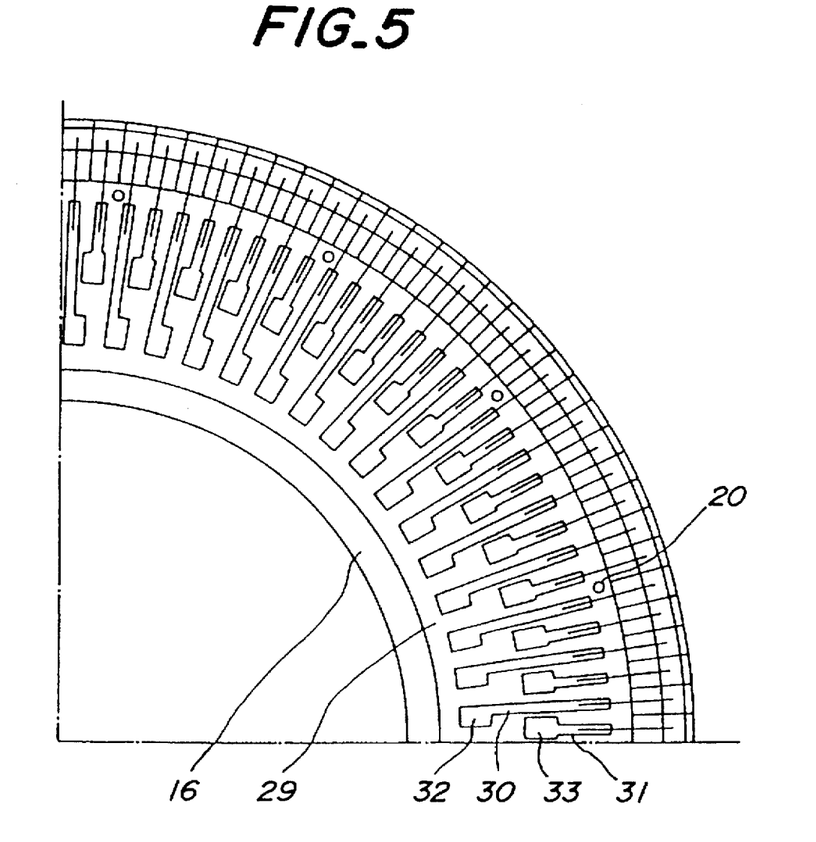
FIG. 5 is a fragmentary end view showing an upper surface of the ultrasonic transducer of the ultrasonic probe of a second embodiment according to the present invention.
Figure 6:
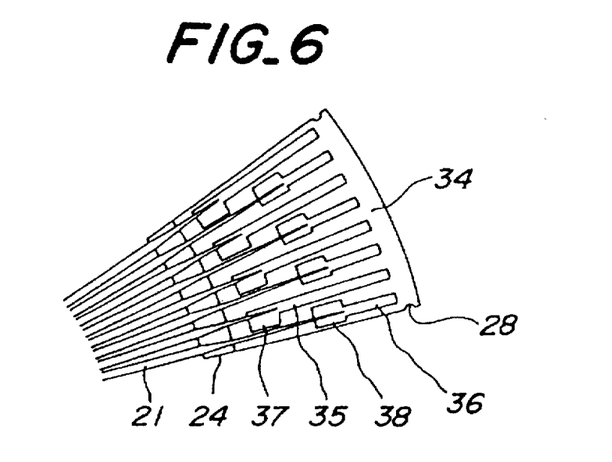
FIG. 6 is an explanatory view showing a series of coaxial cables with a fan type flexible substrate of the ultrasonic probe of the second embodiment according to the present invention.

FIG. 5 is a plan view showing the upper surface of the ultrasonic transducer of the ultrasonic probe according to the second embodiment, and FIG. 6 is a detailed explanatory view showing a series of coaxial cables with the fan shaped flexible substrate of the ultrasonic probe according to the second embodiment. Since each of the portions not shown in FIGS. 5 and 6 is the same as the construction shown in the first embodiment, its explanation is omitted.

In the second embodiment, as shown in FIG. 5, doughnut shaped substrate 29 is provided with two kinds of signal patterns 30 and 31 each having different length in the diametrical direction, alternately. These signal patterns 30, 31 are provided at its central side tip with contacting points 32, 33. While, as shown in FIG. 6, a fan shaped flexible substrate 34 is provided with two kinds of signal patterns 35 and 36 each having a different length in the diametrical direction, alternately. Signal patterns 35, 36 of the fan shaped flexible substrate 34 have the same pitch as that of the signal patterns of the doughnut shaped substrate 29. These signal patterns 35, 36 are provided at its central tip end with contacting points 37, 38.

Then, in the second embodiment, the connection method of the coaxial cable is explained with reference to FIGS. 5 and 6. In this case, the coaxial cable 21 is connected to the fan shaped flexible substrate 34 in the same manner as in FIG. 3 (i.e., through soldering or welding using conductive adhesive material).

Firstly, the coaxial cable 21 with flexible substrate is extended through the hole of the central portion of the ultrasonic transducer 1 and is projected from the central portion of the doughnut shaped substrate 14. Then, the positioning semicircular holes 28 of the fan shaped flexible substrate 34 shown in FIG. 6 are fitted onto the positioning projections 20 of the doughnut shaped substrate 29 shown in FIG. 5, and then the contacting points 37, 38 of the fan shaped flexible substrate 34 are electrically connected to the contacting points 32, 33 of the doughnut shaped substrate 29 so as to superimpose these contacting points to each other by soldering or welding them with a conductive adhesive material. Moreover, the ground pattern 24 of the fan shaped flexible substrate 34 is electrically connected to the ground pattern 16 of the doughnut shaped substrate 29 by soldering or welding them with a conductive adhesive material.

After the above-mentioned steps, as shown in FIG. 1, the ultrasonic transducer according to the second embodiment can obtain the function and effect of the electronic radial type ultrasonic transducer having fine pitch of the element as shown in FIG. 1.

Figure 7:
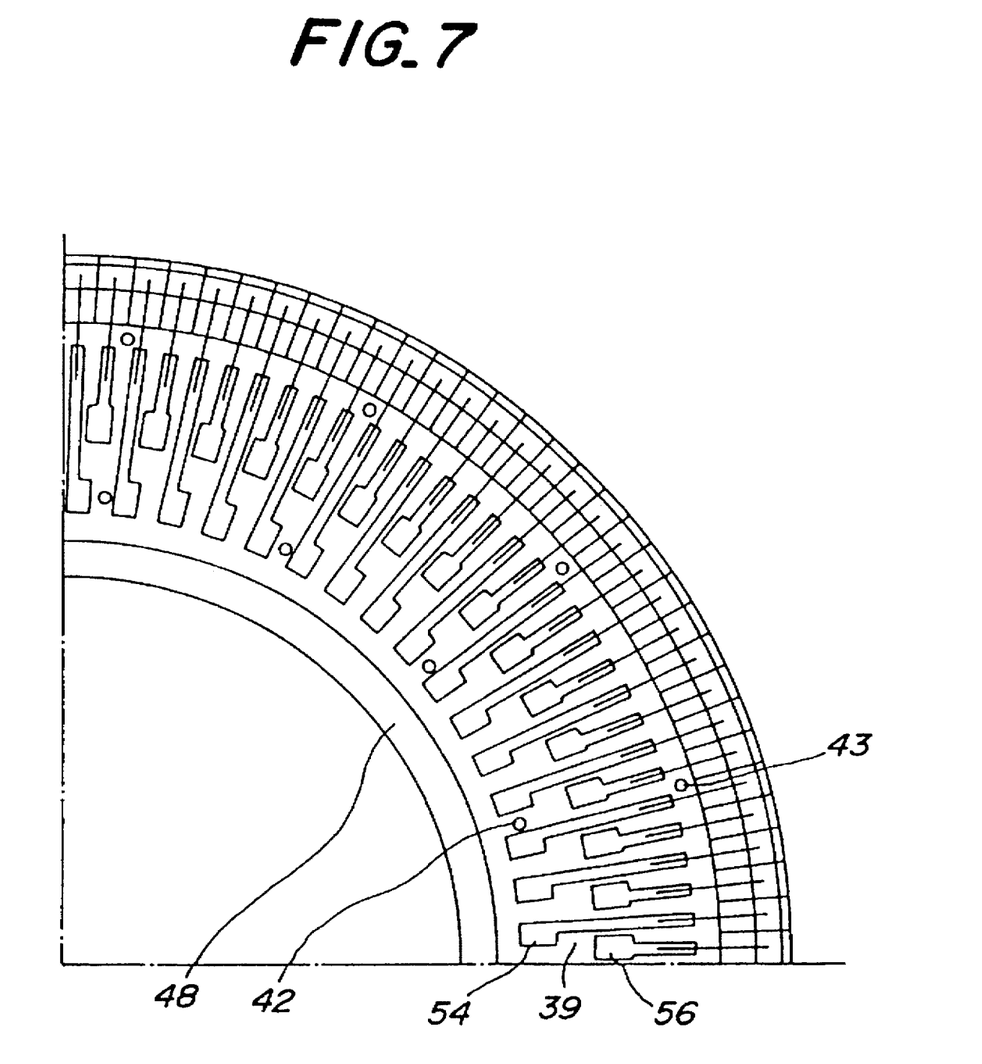
FIG. 7 is a fragmentary end view showing an upper surface of the ultrasonic transducer of a third embodiment of the ultrasonic probe according to the present invention.
Figure 8:
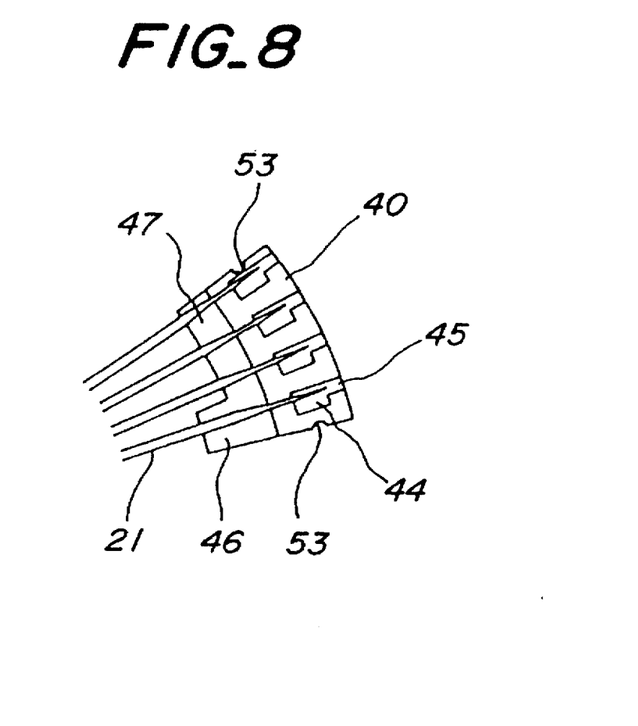
FIG. 8 is an explanatory view showing a series of coaxial cables with a small fan flexible substrate of the third embodiment of the ultrasonic probe according to the present invention.
Figure 9:
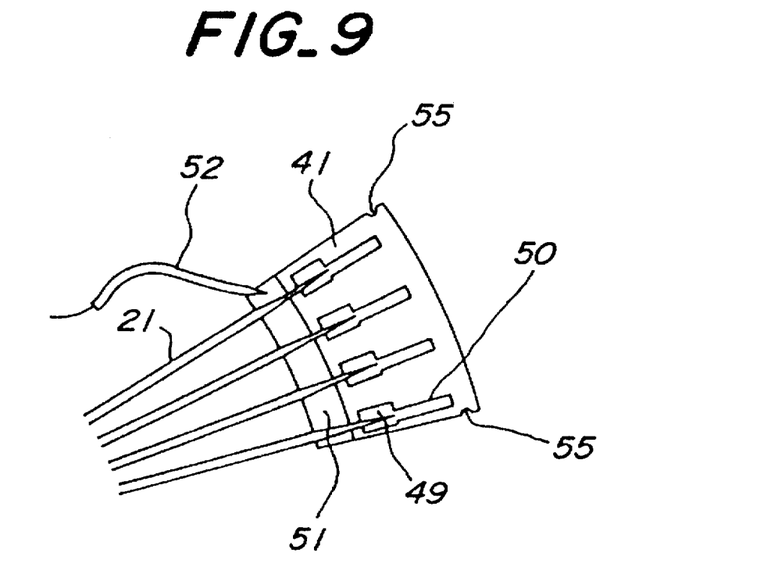
FIG. 9 is an explanatory view showing a series of coaxial cables with a large fan flexible substrate of the third embodiment of the ultrasonic probe according to the present invention.

FIG. 7 is a plan view showing the upper surface of the ultrasonic transducer of the ultrasonic probe according to the third embodiment, FIG. 8 is a detailed explanatory view showing a series of coaxial cables with the small fan shaped flexible substrate of the ultrasonic probe according to the third embodiment, and FIG. 9 is a detailed explanatory view showing a series of coaxial cables with the large fan shaped flexible substrate of the ultrasonic probe according to the third embodiment. Since each of the portions not shown in FIGS. 7, 8 and 9 is the same as the construction shown in the first embodiment, its explanation is omitted.

In this third embodiment, the doughnut shaped substrate 39 shown in FIG. 7 is provided with positioning projections 42, 43 for the small fan shaped flexible substrate 40 shown in FIG. 8, and the large fan shaped flexible substrate 41 shown in FIG. 9 in the peripheral direction with a certain distance, respectively. As shown in FIG. 8, the small fan shaped flexible substrate 40 is provided with signal patterns 45 having the contacting points 44 radially and equidistantly. These signal patterns 45 have pitches having two times as large as the element pitch of the ultrasonic transducer. The small fan shaped flexible substrate 40 is provided at its central side end portion with ground pattern 47 having projections 46. The projections 46 of the ground pattern 47 are to perform electrical connection to the ground pattern 48 of the doughnut shaped substrates 39. This projection 46 can perform conduction to rear surface of the small fan flexible substrate 40, but the other ground pattern 47 can not be connected to the rear surface of the small fan flexible substrate 40.

As shown in FIG. 9, the large fan shaped flexible substrate 41 is provided with signal patterns 50 having contacting points 49 printed radially and equidistantly and these signal patterns 50 have pitches having two times as large as the element pitch of the ultrasonic transducer. The large fan shaped flexible substrate 41 is provided at its central side end portion with ground pattern 51 printed thereon and the ground pattern 51 can not be connected to the rear surface of the large fan flexible substrate 41. The ground pattern 51 is electrically connected to lead wires 52 by soldering or welding them with a conductive adhesive material.

Then, the connection method of the coaxial cable in the third embodiment is explained with reference to FIGS. 7 to 9.

At the first time, as shown in FIGS. 8 and 9, the coaxial cable 21 is electrically connected to the fan shaped flexible substrates 40 and 41, respectively, by soldering or welding them with a conductive adhesive material. Then, the small fan shaped flexible substrate 40 and the large fan shaped flexible substrate 41 are extended through the central portion of the ultrasonic transducer 1 and projected from the central portion of the doughnut shaped substrate 14. Next, the contacting points 44 of the small fan shaped flexible substrate 40 and the contacting points 54 of the doughnut shaped substrate 39 are electrically connected by and soldering or welding them with a conductive adhesive material at the position of which the positioning semicircular holes 53 of the small fan shaped flexible substrate 40 are fitted onto the positioning projections 42 of the doughnut shaped substrate 39. Moreover, the projection portion 46 of the small fan shaped flexible substrate 40 and the ground pattern 48 of the doughnut shaped substrate 39 are electrically connected by soldering or welding them with a conductive adhesive material.

Then, the contacting points 49 of the large fan shaped flexible substrate 41 and the contacting points 56 of the doughnut shaped substrate 39 are electrically connected by soldering or welding them using a conductive adhesive material at the position of which the positioning semicircular holes 55 of the large fan shaped flexible substrate 41 are fitted onto the positioning projections 43 of the doughnut shaped substrate 39. Next, the un-welded end portion not welded of the lead wire 52 of the large fan shaped flexible substrate 41 is electrically connected to the ground pattern 48 of the doughnut shaped substrate 39 by soldering or welding them using a conductive adhesive material.

After the above-mentioned steps, as shown in FIG. 1, the cap 2 is welded to the ultrasonic transducer 1, thereby completing the assembly of the ultrasonic transducer 1 to its tip hard portion 5.

The ultrasonic transducer 1 according to the third embodiment can obtain the function and effect shown in the second embodiment, and thus it is possible to set the pitch of the signal pattern of the fan shaped flexible substrates 40 and 41 widely.

Figure 10:
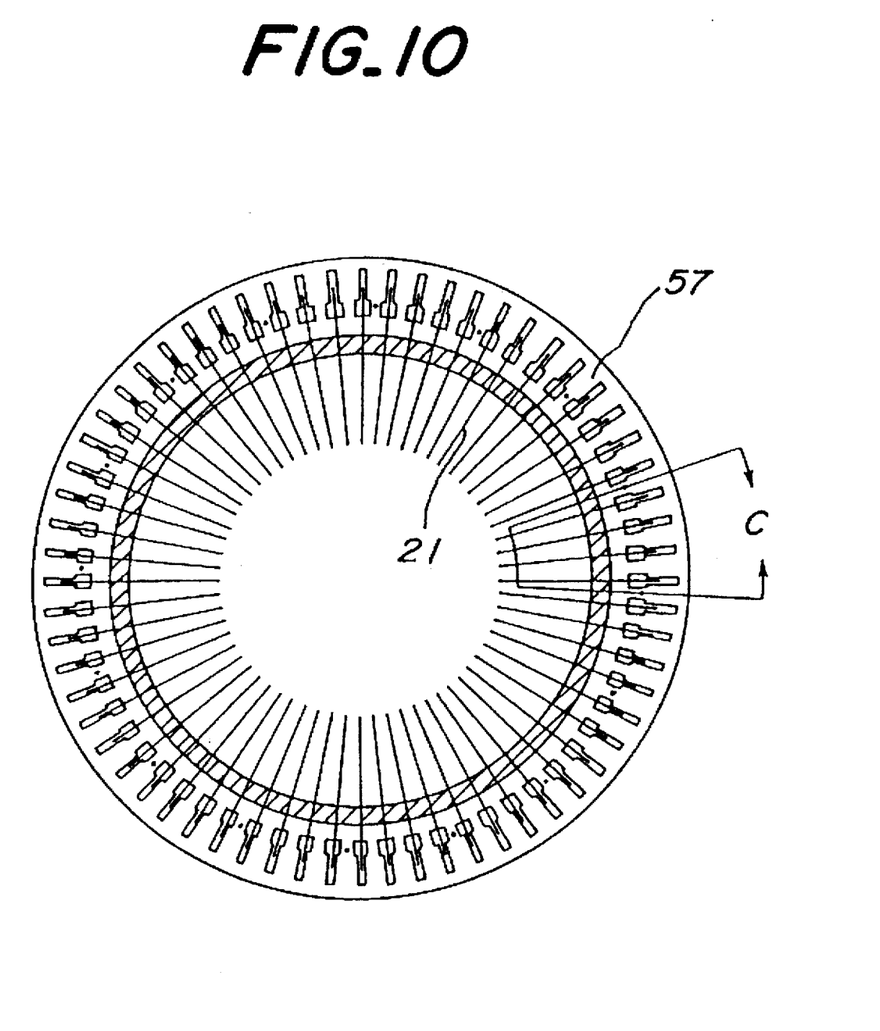
FIG. 10 is an end view showing whole doughnut flexible substrate of a fourth embodiment ultrasonic probe of according to the present invention.
Figure 11A:
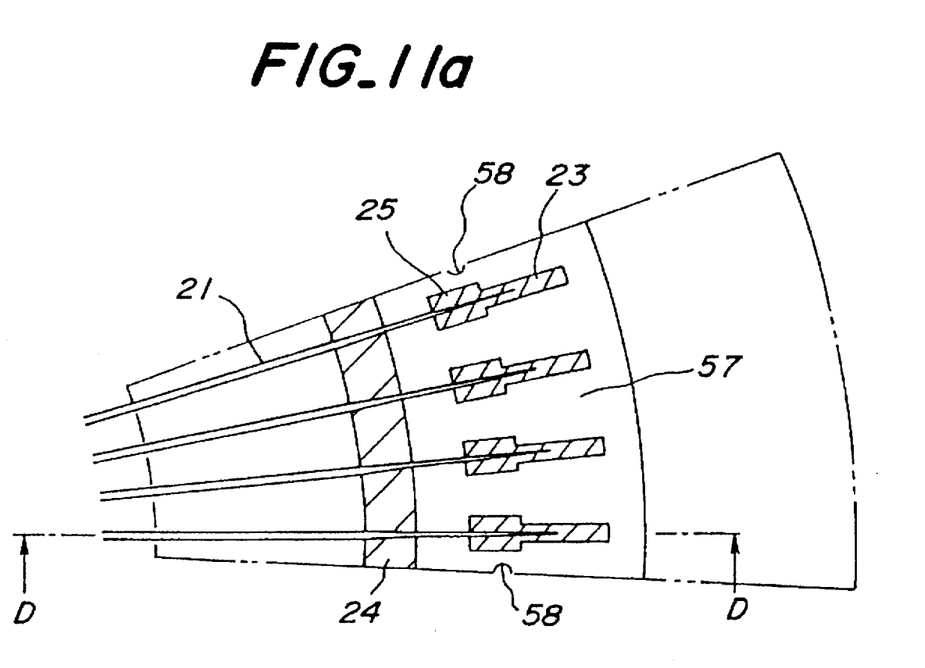
FIG. 11a is a series of a coaxial cable with a flexible substrate for using the ultrasonic probe according to the present invention and a detailed explanatory view of an enclosed portion C shown in FIG. 10.
Figure 11B:
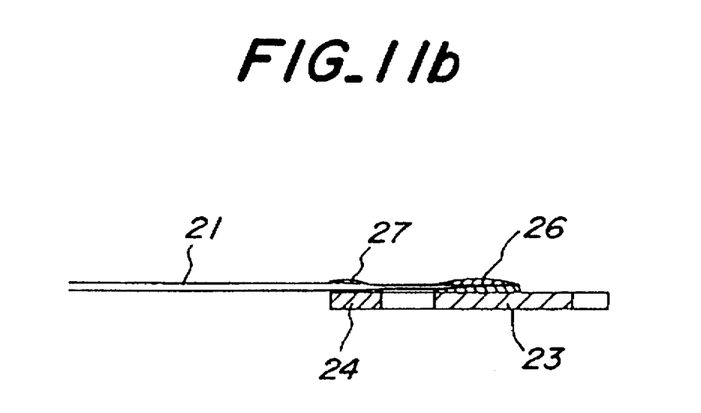

FIG. 10 is a plan view showing whole of doughnut shaped flexible substrate of the ultrasonic probe according to a fourth embodiment of the present invention. FIG. 11a is a detailed explanatory view of an enclosed portion C shown in FIG. 10, and FIG. 11b is a cross-sectional view taken on line D—D of FIG. 11a. Since each of the portions not shown in FIGS. 10, 11a and 11b is the same as the construction shown in the first embodiment, its explanation is omitted.

As shown in FIG. 10, the doughnut shaped flexible substrate 57 of the ultrasonic probe according to the fourth embodiment is formed by combining side straight portions of the fan shaped flexible substrate 22 of the first embodiment integrally in the form of doughnut shape. In FIG. 3 in the first embodiment, the fan shaped flexible substrate 22 is provided with the positioning semicircular hole 28, but in this embodiment, as shown in FIG. 11a, an positioning hole 58 is provided instead of the positioning semicircular hole 28.

The connection method of the coaxial cable in the fourth embodiment is explained with reference to FIGS. 10, 11a and 11b.

As shown in FIGS. 10, 11a and 11b, the coaxial cable 21 is electrically connected to the doughnut shaped flexible substrate 57 by soldering or welding them with a conductive adhesive material. Then, the doughnut shaped flexible substrate 57 is extended through the central portion of the ultrasonic transducer 1, thereby projecting it from the central portion of the doughnut shaped substrate 14. Next, ground pattern 24 of the doughnut shaped flexible substrate 57 is electrically connected to the ground pattern 16 of the doughnut shaped substrate 14 by soldering or welding them with a conductive adhesive material, while performing given positioning by the positioning holes 58.

After the above-identified steps, as shown in FIG. 1, the cap 2 is welded to the ultrasonic transducer 1, thereby completing the assembly of the ultrasonic transducer 1 to its tip hard portion 5.

According to the ultrasonic probe of the fourth embodiment, it has superior assemblage and repairability in construction rather than those of the first embodiment, and the connection points of the cable are disposed between the ultrasonic transducer 1 and the cap section 2, so that the outer diameter of the tip hard section of the endoscope and the length of the tip hard section can be decreased.

Figure 12A:
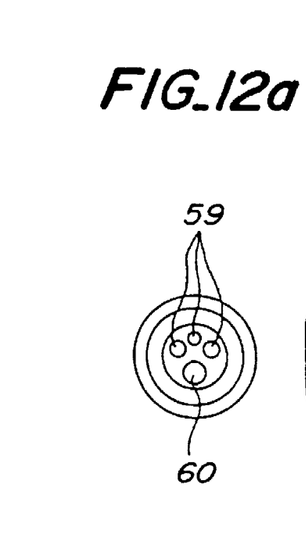
FIG. 12a is a front view showing a construction of a tip insertion section of a fifth embodiment of the ultrasonic probe according to the present invention.
Figure 12B:
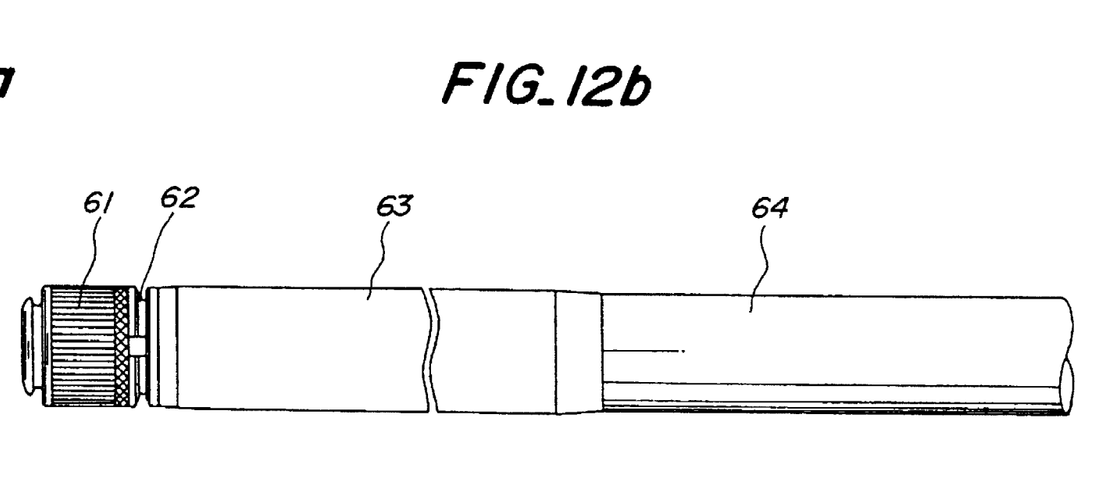
FIG. 12b is a side view showing a construction of a tip insertion section of the fifth embodiment of the ultrasonic probe according to the present invention.

FIGS. 12a and 12b are views each showing a construction of a tip insertion section of a fifth embodiment of the ultrasonic probe according to the present invention. The ultrasonic probe of this embodiment is provided to the insertion section of an ultrasonic endoscope of the electronic radial type and as shown in FIG. 12a, a direct forward-viewing optical observation system 59 and an air/water supply channel 60 are arranged at tip portion of the ultrasonic probe. As shown in FIG. 12b, the ultrasonic transducer 61 is arranged at the back of the optical observation system 59. An operating side portion of the tip hard section is provided with a balloon water supply channel 62, a bending section 63, and a flexible tube 64, in that order. The construction of the other portion is the same as that of the first to fourth embodiments, so that according to this embodiment, the connection method of the cable to the ultrasonic probe having the electronic radial ultrasonic transducer with superior assemblage/repairability and the electronic radial ultrasonic endoscope having short length of the tip hard section can be obtained.

The connection method of coaxial cable in the fifth embodiment is the same as that of the first to fourth embodiment. Moreover, the function and effect of the fifth embodiments are the same as those of the first to fourth embodiments.

Figure 13A:
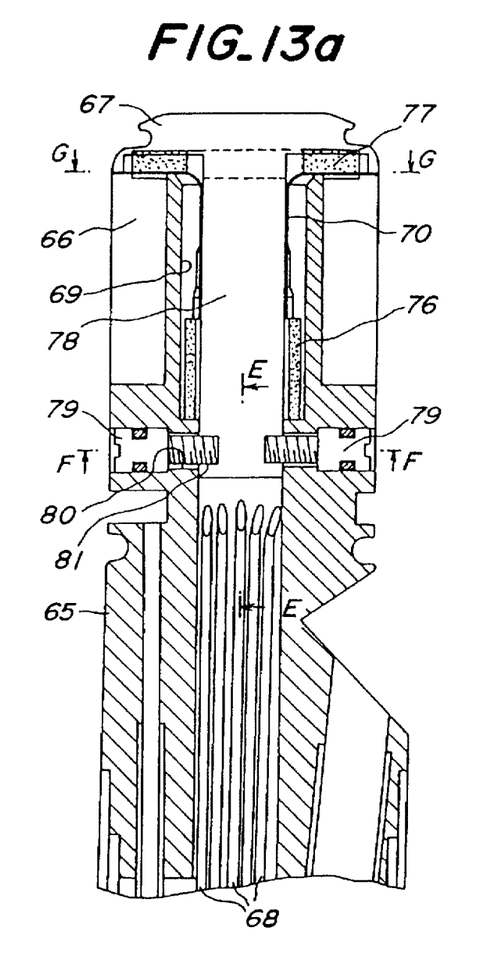
FIG. 13a is a cross-sectional view showing a construction of a tip insertion section of a sixth embodiment of an ultrasonic probe according to the present invention.
Figure 13B:
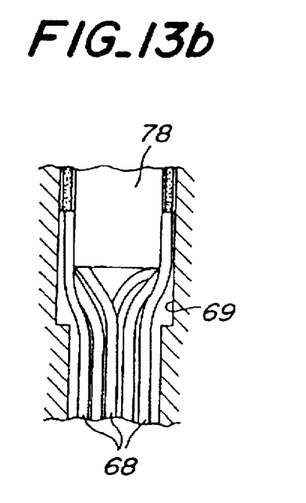
Figure 13C:
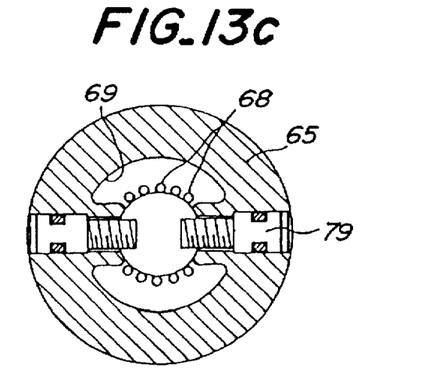

FIG. 13a is a cross-sectional view showing a construction of a tip insertion section of a sixth embodiment of an ultrasonic probe according to the present invention. FIG. 13b is a cross-sectional view taken on line E—E of FIG. 13a, and FIG. 13c is a cross-sectional view taken on line F—F of FIG. 13a. The ultrasonic probe of this embodiment is provided to the insertion section of an ultrasonic endoscope of a forward-and oblique-viewing electronic radial type and its tip insertion section comprises a hard section 65 as a main member, an ultrasonic transducer 66, and a tip cap section 67. The construction of the other portion not explained in this embodiment is the same as that of the first to fifth embodiments, so that according to this embodiment, the connection method of the cable to the ultrasonic probe having the electronic radial ultrasonic transducer with superior assemblage/repairability and the fixing method capable of preventing removal of the cable and the flexible substrate from the ultrasonic transducer can be obtained.

That is, in this embodiment, a group of coaxial cable 68 from the connecting connector for the ultrasonic observation device (not shown) are extended to the hard section 65 in the same manner as in the first to fifth embodiments. In this embodiment, also, the coaxial cable groups 68 are connected to lower end portion of the flexible substrates 70 in an axial circular hole 69 of the hard section 65. The upper end portion of the flexible substrate 70 extended through the circular hole 69 is bent in the diameter direction and the bent portion thereof is extended to the doughnut shaped substrate 71 disposed thereon (refer to FIG. 14a).

Figure 14A:
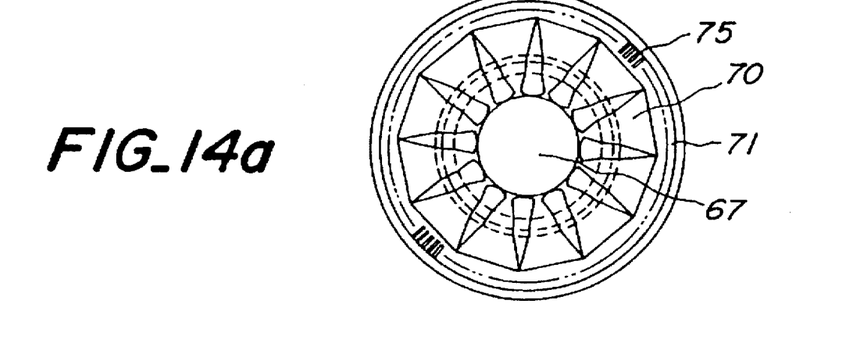
FIG. 14a is a front view showing a flexible substrate taken on line G—G of FIG. 13a and a doughnut shaped substrate shown in the sixth embodiment.
Figure 14B:
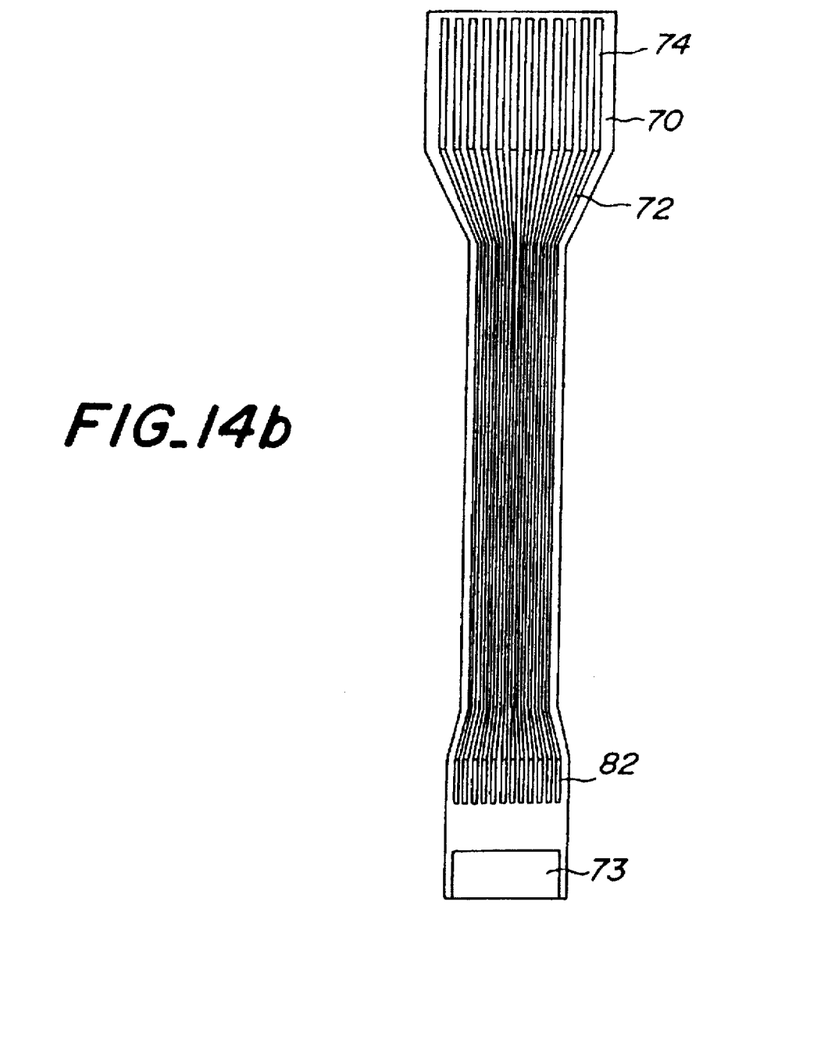
FIG. 14b is a detailed pattern printed on the upper surface of the flexible substrate.

FIG. 14a shows a flexible substrate 70 and a doughnut shaped substrate 71 of the sixth embodiment and is a sectional view taken substantially along the lines G—G of FIG. 13a. FIG. 14b is a detailed pattern printed on the upper surface of the flexible substrate 70. As shown in FIG. 14b, the flexible substrate 70 is provided its upper surface with a plurality of signal patterns 72, land portions 74 and 82 lead to both ends of respective signal patterns 72 and ground pattern 73. Ground signal lines (not shown) of the coaxial cable groups 68 are connected to the ground pattern 73, and signal lines (not shown) of the coaxial cable groups 68 are connected to land portions 82 of the signal patterns 72. Land portions 74 of the signal patterns 72 are electrically connected to the signal patterns 72 provided whole periphery of the end portion of the doughnut shaped pattern 71 with wire bonding or the like.

Then, in the cable connection method according to the first to fifth embodiments, when the insertion portion of the ultrasonic probe is bent, the coaxial cable is drawn within the inserting portion, so that there is a fear of removing the coaxial cable from the ultrasonic transducer. In this embodiment, as a countermeasure thereof, the coaxial cable group 69 and the flexible substrate 70 are fixed by means of rubber members 76 and 77, respectively, so as not to remove the coaxial cable group 68 and the flexible substrate 70 from the tip inserting section of the ultrasonic probe.

That is, the coaxial cable group 68 is fixed onto the outer periphery surface portion of the small cylindrical portion 78 of the tip cap section 67 by the first rubber member 76. The upper end portion bent in the radial direction of the flexible substrate 70 is fixed onto the doughnut shaped substrate 71 with the flexure of the second rubber member 77 by registering the positions of radial holes 80 provided in the large cylindrical portion of the hard section 65 and screw holes 81 provided in the small cylindrical portion of the tip cap section 67 and by fixing the tip cap section 67 to the hard section 65 through the doughnut shaped substrate 71 and the second rubber member 77 with water-tight screws 79. The second rubber member 77 serves also as a member for positively holding between the small diameter portion of the hard section 65 and the tip cap 67 in the water-tight condition.

Moreover, in this embodiment, the hard section is constructed so as to hold the ultrasonic transducer 66 on the small diameter portion thereof, but as shown in FIG. 13a, the upper portion from the lower notch portion of the hole 80 of the hard section 65 may be used as another member.

Then, the method of interchanging the ultrasonic transducer and the coaxial cable in the sixth embodiment is explained with reference to FIGS. 13a and 13b.

In case of performing the interchanging of the ultrasonic transducer, at first, the water-tight screws 79 are removed in the outer periphery direction as shown in FIGS. 13a, 13c, the tip cap 67 and the rubber member 77 are raised to the upper direction and removed as shown in FIG. 13a, the wire bonding for connecting the doughnut shaped substrate 71 and the signal patterns 75 of the flexible substrate 70 is removed, and then the fault ultrasonic transducer 66 is took out and interchanged to new ultrasonic transducer 66. In case of interchanging the coaxial cable groups 68, also, in the same manner as in the above, the water-tight screws 79 are removed, the tip cap 67 and the rubber member 77 are removed, the wire bonding for connecting the doughnut shaped substrate 71 and the signal patterns 75 of the flexible substrate 70 is removed, and the coaxial cable group 68 is pulled out and then new coaxial cable group 68 is interchanged.

According to the ultrasonic probe of the sixth embodiment, it is possible to provide a method of connecting the cable to the electronic radial ultrasonic transducer having superior assemblage and repairability in construction by connecting the ultrasonic transducer 66 and the coaxial cable group 68 through the flexible substrate 70 and the doughnut shaped substrate 71.

It is also possible to provide a fixing method capable of preventing removal of the cable and the flexible substrate from the ultrasonic transducer by fixing coaxial cable group 68 with the rubber members 76, 77.

It is to be understood by those skilled in the art that the forgoing description is a preferred embodiment of the disclosed device and that various changes and modifications may be made in the invention without departing from the spirit and scope thereof. For example, the cable groups connected to the signal pattern of the substrate may be disposed inner side of the doughnut shaped substrate. At least one substrate having patterns formed so as to conduct opposite to respective signal patterns of the doughnut shaped substrate may be a flexible substrate. The signal patterns of the doughnut shaped substrate may be arranged radially. The form of the substrate may be a fan shape, a paper tablet shape or a doughnut shape.

The electrical connection of the substrate or the doughnut shaped substrate may be performed by soldering or welding them with a conductive adhesive material or by welding the cap provided at the tip portion in the inserting direction of the electronic radial transducer. The cable may be a coaxial cable having an outer diameter of less than 0.3 mm. The form of the fan shaped flexible substrate according to the first to the third embodiments may be a paper tablet shape.

The ultrasonic probe according to the sixth embodiment was applied to the ultrasonic endoscope of the front taper electronic radial type, but the applying range of the ultrasonic probe of the sixth embodiment is not limited thereto. For example, the optical system and the channels of the ultrasonic endoscope may be arranged within the cylindrical portion 78 of the tip cap 67 of the ultrasonic probe according to this embodiment, thereby applying to the ultrasonic endoscope of the direct-vision electronic radial type, decreasing the length of the tip hard section of the ultrasonic endoscope, or applying the electronic radial ultrasonic probe without providing endoscopic function.

What is claimed is:

1. An ultrasonic probe having an electronic radial transducer, said probe comprising:

a plurality of piezoelectric elements each having electrodes provided on surfaces thereof;

an annular supporting member axially positioned beneath said elements to radially support said elements;

a doughnut-shaped substrate having a plurality of first connection pads arranged in a signal pattern, said doughnut-shaped substrate being axially positioned beneath side edges of said elements; and an overlapping substrate having a plurality of second connection pads arranged in accordance with said signal pattern, said overlapping substrate being axially superposed onto said doughnut-shaped substrate, wherein said second connection pads, said first connection pads, and said electrodes of said elements are electrically connected.

2. An ultrasonic probe as claimed in claim 1, wherein a plurality of signal cables connected to the overlapping substrate are disposed on an inner side of the doughnut shaped substrate.

3. An ultrasonic probe as claimed in claim 2, wherein said first connection pads of the doughnut shaped substrate are disposed in a radial configuration.

4. An ultrasonic probe as claimed in claim 2, wherein at least one of the substrates has patterns formed so as to conduct opposite to respective signal patterns of the doughnut shaped substrate and is a flexible substrate.

5. An ultrasonic probe as claimed in claim 4, wherein said first connection pads of the doughnut shaped substrate are disposed in a radial configuration.

6. An ultrasonic probe as claimed in claim 2, wherein the shape of the overlapping substrate is a fan shape, a paper-stripe shape, or a doughnut shape.

7. An ultrasonic probe as claimed in claim 2, wherein the fixings of the overlapping substrate and the doughnut shaped substrate are performed by soldering or welding using a conductive adhesive.

8. An ultrasonic probe as claimed in claim 2, wherein the probe further comprises:

a tip hard section having a first cylindrical portion, an axial cylindrical opening, and a second cylindrical portion, and a tip cap section which is inserted and fitted into said axial cylindrical opening of the tip hard section, wherein the diameter of said second cylindrical portion is small than the diameter of said first cylindrical portion, and said ultrasonic transducer is fitted onto said second cylindrical portion, and wherein portions of the signal cables within the axial cylindrical opening of the tip hard section are fixed onto the outer peripheral surface of the second cylindrical portion by a first rubber member, and portions of the signal cables which are bent in the radial direction of the overlapping substrate are fixed to the doughnut shaped substrate by the tip cap section via a second rubber member.

9. An ultrasonic probe as claimed in claim 2, wherein the cable is a coaxial cable having an outer diameter of less than 0.3 mm.

10. An ultrasonic probe as claimed in claim 1, wherein said overlapping substrate is a flexible substrate.

11. An ultrasonic probe as claimed in claim 10, wherein said first connection pads of the doughnut shaped substrate are disposed in a radial configuration.

12. An ultrasonic probe as claimed in claim 1, wherein the shape of the overlapping substrate is a fan shape, a paper-stripe shape, or a doughnut shape.

13. An ultrasonic probe as claimed in claim 1, wherein the fixings of the overlapping substrate and the doughnut shaped substrate are performed by soldering or welding using a conductive adhesive.

14. An ultrasonic probe as claimed in claim 1, wherein the probe further comprises:

a tip hard section having a first cylindrical portion, an axial cylindrical opening, and a second cylindrical portion, and a tip cap section which is inserted and fitted into said axial cylindrical opening of the tip hard section, wherein the diameter of said second cylindrical portion is smaller than the diameter of said first cylindrical portion, and said ultrasonic transducer is fitted onto said second cylindrical portion, and wherein portions of the signal cables withinin the axial cylindrical opening of the tip hard section are fixed onto the outer peripheral surface of the second cylindrical portion by a first rubber member, and portions of the signal cables which are bent in the radial direction of the overlapping substrate are fixed to the doughnut shaped substrate by the tip cap section via a second rubber member.

15. An ultrasonic probe as claimed in claim 1, wherein the cable of the substrates has patterns formed so as to conduct opposite to respective signal patterns of the doughnut shaped substrate and is a flexible substrate.

* * * * *